(12) United States Patent
Smith (10) Patent No.: US 12,251,364 B2
(45) Date of Patent: Mar. 18, 2025

(54) TREATING NON-ALCOHOLIC STEATOHEPATITIS WITH CCK INHIBITORS

(71) Applicant: GEORGETOWN UNIVERSITY, Washington, DC (US)

(72) Inventor: Jill P. Smith, Camp Hill, PA (US)

(73) Assignee: Georgetown University, Washington, DC (US)

( * ) Notice: Subject to any disclaimer, the term of this patent is extended or adjusted under 35 U.S.C. 154(b) by 901 days.

(21) Appl. No.: 17/291,681

(22) PCT Filed: Nov. 5, 2019

(86) PCT No.: PCT/US2019/059833
§ 371 (c)(1),
(2) Date: May 6, 2021

(87) PCT Pub. No.: WO2020/097054
PCT Pub. Date: May 14, 2020

(65) Prior Publication Data
US 2022/0000819 A1    Jan. 6, 2022

Related U.S. Application Data

(60) Provisional application No. 62/756,384, filed on Nov. 6, 2018.

(51) Int. Cl.
*A61K 31/197*    (2006.01)
*A61K 31/355*    (2006.01)
*A61P 1/16*    (2006.01)

(52) U.S. Cl.
CPC .......... *A61K 31/197* (2013.01); *A61K 31/355* (2013.01); *A61P 1/16* (2018.01)

(58) Field of Classification Search
CPC .. A61K 31/197; A61K 31/355; A61K 31/195; A61K 31/5513; A61K 45/06; A61K 2300/00; A61P 1/16
USPC ........................................................ 514/563
See application file for complete search history.

(56) References Cited

U.S. PATENT DOCUMENTS

| | | | |
|---|---|---|---|
| 3,710,795 | A | 1/1973 | Higuchi et al. |
| 4,863,457 | A | 9/1989 | Lee |
| 5,501,856 | A | 3/1996 | Ohtori et al. |
| 2008/0241223 | A1 | 10/2008 | Nivaggioli et al. |
| 2009/0312302 | A1 | 12/2009 | Currie |
| 2018/0079820 | A1* | 3/2018 | Yan .................... C07K 16/2869 |

FOREIGN PATENT DOCUMENTS

| | | |
|---|---|---|
| EP | 0430539 | 6/1991 |
| EP | 0488401 | 6/1992 |
| WO | 2005011665 | 2/2005 |
| WO | 2011138421 | 11/2011 |
| WO | 2018170254 | 9/2018 |
| WO | WO-2018170254 A1 * | 9/2018 ........... A61K 31/198 |

OTHER PUBLICATIONS

Banini, Current Opinion in Gastroenterology, vol. 33, No. 3, May 2017, pp. 134-141, "Current and Future Pharmacologic Treatment of Nonalcoholic Steatohepatitis" (Year: 2017).*
Berna et al. Current Topics in Medicinal Chemistry, vol. 7, No. 12, 2007, pp. 1211-1231, "Role of CCK/Gastrin Receptors in Gastrointestinal/Metabolic Diseases and Results of Human Studies Using Gastrin/CCK Receptor Agonists/Antagonists in these Diseases" (Year: 2007).*
Sanyal et al, The New England Journal of Medicine, vol. 362, No. 18, May 6, 2010, pp. 1675-1685, "Pioglitazone, Vitamin E, or Placebo for Nonalcoholic Steatohepatitis" (Year: 2010).*
Kucera et al. World J Gastroenterol Jul. 14, 2014; 20(26): 8364-8376, "Experimental models of non-alcoholic fatty liver disease in rats" (Year: 2014).*
Nadella et al. American Journal of Physiology-Gastrointestinal and Liver Physiology, 315: G699-G712, 2018. first published Jun. 21, 2018; doi:10.1152/ajpgi.00123.2018.0193-1857/18, (Year: 2018).*
Fujiwara et al. Journal of Hepatology 2018, vol. 68, p. 526-549, "Risk factors and prevention of hepatocellular carcinoma in the era of precision medicine" (Year: 2018).*
Gay et al. Proceedings of the American Association for Cancer Research Annual Meeting 2019; Mar. 29-Apr. 3, 2019; Atlanta, GA. Philadelphia (PA): MGR; Cancer Res 2019;79(13 Suppl):Abstract nr 2728. (Year: 2019).*
Akinyemiju et al., "The Burden of Primary Liver Cancer and Underlying Etiologies From 1990 to 2015 at the Global, Regional, and National Level: Results From the Global Burden of Disease Study 2015", JAMA Oncology, vol. 3, No. 12, Global Burden of Disease Liver Cancer Collaboration, Dec. 1, 2017, pp. 1683-1691.
Aleman et al., "Mechanisms of Obesity-Induced Gastrointestinal Neoplasia", Gastroenterology, vol. 146, 2014, pp. 357-373.
Apte et al., "Desmoplastic Reaction in Pancreatic Cancer: Role of Pancreatic Stellate Cells", Pancreas, vol. 29, No. 3, Oct. 2004, pp. 179-187.
Arem et al., "Dietary Fat Intake and Risk of Pancreatic Cancer in the Prostate, Lung, Colorectal and Ovarian Cancer Screening Trial", Annals of Epidemiology, vol. 23, 2013, pp. 571-575.
Banini et al., "Current and Future Pharmacologic Treatment of Nonalcoholic Steatohepatitis", Current Opinion in Gastroenterology, vol. 33, No. 3, May 2017, pp. 134-141.
Ben-Harosh et al., "Pancreatic Stellate Cell Activation is Regulated by Fatty Acids and ER Stress", Experimental Cell Research, vol. 359, 2017, pp. 76-85.
Berger , "Obesity and Cancer Pathogenesis", Annals of the New York Academy of Sciences, vol. 1311, 2014, pp. 57-76.
Berna et al., "CCK1 and CCK2 Receptors are Expressed on Pancreatic Stellate Cells and Induce Collagen Production", The Journal of Biological Chemistry, vol. 285, No. 50, Dec. 10, 2010, pp. 38905-38914.

(Continued)

*Primary Examiner* — Jared Barsky
*Assistant Examiner* — Liyuan Mou
(74) *Attorney, Agent, or Firm* — Kilpatrick Townsend & Stockton LLP (57) ABSTRACT

Provided herein are methods for treating nonalcoholic steatohepatitis (NASH) in a subject, comprising administering to a subject having NASH an effective amount of a CCK receptor inhibitor.

10 Claims, 8 Drawing Sheets

(56) References Cited

OTHER PUBLICATIONS

Berna et al., "Role of CCK/Gastrin Receptors in Gastrointestinal/Metabolic Diseases and Results of Human Studies Using Gastrin/CCK Receptor Agonists/Antagonists in these Diseases", Current Topics in Medicinal Chemistry, vol. 7, No. 12, 2007, pp. 1211-1231.
Bister et al., "Increased Expression of Matrix Metalloproteinases-21 and -26 and TIMP-4 in Pancreatic Adenocarcinoma", Modern Pathology, vol. 20, 2007, pp. 1128-1140.
Boj et al., "Organoid Models of Human and Mouse Ductal Pancreatic Cancer", Cell, vol. 160, Jan. 15, 2015, pp. 1-15.
Bracci, "Obesity and Pancreatic Cancer: Overview of Epidemiologic Evidence and Biologic Mechanisms", Molecular Carcinogenesis, vol. 51, 2012, pp. 53-63.
Brandi et al., "Microbiota, Nash, Hcc and the Potential Role of Probiotics", Carcinogenesis, vol. 38, No. 3, Mar. 1, 2017, pp. 231-240.
Camilleri, "Peripheral Mechanisms in Appetite Regulation", Gastroenterology, vol. 148, No. 6, May 2015, pp. 1219-1233.
Chandra et al., "Immunoglobulin-Like Domain Containing Receptor 1 Mediates Fat-Stimulated Cholecystokinin Secretion", Journal of Clinical Investigation, vol. 123, No. 8, Aug. 2013, pp. 3343-3352.
Chang et al., "Characterization of the Binding of [3H]-(+/-)-L-364,718: a New Potent, Nonpeptide Cholecystokinin Antagonist Radioligand Selective for Peripheral Receptors", Molecular Pharmacology, vol. 30, No. 3, Sep. 1986, pp. 212-217.
Corbett et al., "Induction and Chemotherapeutic Response of Two Transplantable Ductal Adenocarcinomas of the Pancreas in C57BL/6 Mice", Cancer Research, vol. 44, Feb. 1984, pp. 717-726.
Coussens et al., "Inflammation and Cancer", Nature, vol. 420, No. 6917, Dec. 19, 2002, pp. 1-18.
Cox et al., "Molecular Pathways: Connecting Fibrosis and Solid Tumor Metastasis", Clinical Cancer Research, vol. 20, No. 14, Jul. 15, 2014, pp. 3637-3643.
Dawson et al., "High-Fat, High-Calorie Diet Promotes Early Pancreatic Neoplasia in the Conditional KrasG12D Mouse Model", Cancer Prevention Research (Phila), vol. 6, 2013, pp. 1064-1073.
Dockray et al., "Cholecystokinin", Current Opinion in Endocrinology, Diabetes and Obesity, vol. 19, No. 1, Feb. 2007, pp. 8-12.
Dockray, "Luminal Sensing in the Gut: An Overview", Journal of Physiology and Pharmacology, vol. 54, Supplemental 4, 2003, pp. 9-17.
Dufresne et al., "Cholecystokinin and Gastrin Receptors", Physiological Reviews, vol. 86, No. 3, Jul. 2006, pp. 805-847.
Dutta et al., "Leptin and Cancer: Pathogenesis and Therapeutic Modulation", Indian Journal of Endocrinology and Metabolism, vol. 16, 2012, pp. S596-S600.
Elsasser et al., "Time Course and Cellular Source of Pancreatic Regeneration Following Acute Pancreatitis in the Rat", Pancreas, vol. 1, 1986, pp. 421-429.
Estes et al., "Modeling the Epidemic of Nonalcoholic Fatty Liver Disease Demonstrates an Exponential Increase in Burden of Disease", Hepatology, vol. 67, No. 1, Jan. 2018, pp. 123-133.
Fan et al., "Fibroblast Activation Protein (FAP) Accelerates Collagen Degradation and Clearance from Lungs in Mice", Journal of Biological Chemistry, vol. 291, 2016, pp. 8070-8089.
Feig et al., "The Pancreas Cancer Microenvironment", Clinical Cancer Research, vol. 18, 2012, pp. 4266-4276.
Ferrante et al., "Adipocyte-Derived Exosomal miRNAs: A Novel Mechanism for Obesity-Related Disease", Pediatric Research, vol. 77, 2015, pp. 447-454.
Forte et al., "HCL Secretion by the Gastric Oxyntic Cell", In Johnson L, ed., Physiology of the Gastrointestinal Tract, Second Edition, vol. 1, 1987, 13 pages.
Ghadirian et al., "Epidemiology of Pancreatic Cancer: An Overview", Cancer Detection and Prevention, vol. 27, 2003, pp. 87-93.
Gialeli et al., "Roles of Matrix Metalloproteinases in Cancer Progression and Their Pharmacological Targeting", The FEBS Journal, vol. 278, 2011, pp. 16-27.
Gibbons et al., "Postprandial Profiles of CCK after High Fat and High Carbohydrate Meals and the Relationship to Satiety in Humans", Peptides, vol. 77, 2016, pp. 3-8.
Gilbert et al., "Cytokines, Obesity, and Cancer: New Insights on Mechanisms Linking Obesity to Cancer Risk and Progression", Annual Review of Medicine, vol. 64, 2013, pp. 45-57.
Goodwin et al., "Impact of the Obesity Epidemic on Cancer", Annual Review of Medicine, vol. 66, 2015, pp. 281-296.
Gordon-Dseagu et al., "A Cohort Study of Adolescent and Midlife Diet and Pancreatic Cancer Risk in the NIH-AARP Diet and Health Study", American Journal of Epidemiology, vol. 186, 2017, pp. 305-317.
Griffith, "Induction of Tumor Cell Apoptosis by TRAIL Gene Therapy", Methods in Molecular Biology, vol. 542, 2009, pp. 315-334.
Hahne et al., "Proglumide and Benzotript: Members of a Different Class of Cholecystokinin Receptor Antagonists", Proceedings of the National Academy of Sciences, vol. 78, No. 10, Oct. 1981, pp. 6304-6308.
Heinen et al., "Meat and Fat Intake and Pancreatic Cancer Risk in the Netherlands Cohort Study", International Journal of Cancer, vol. 125, 2009, pp. 1118-1126.
Hingorani et al., "Phase Ib Study of PEGylated Recombinant Human Hyaluronidase and Gemcitabine in Patients with Advanced Pancreatic Cancer", Clinical Cancer Research, vol. 22, No. 12, Jun. 15, 2016, pp. 2848-2854.
Honda et al., "Efficacy of Glutathione for the Treatment of Nonalcoholic Fatty Liver Disease: an Open-label, Single-arm, Multicenter, Pilot Study", BMC Gastroenterology, vol. 17, No. 1, Aug. 8, 2017, 8 pages.
Hotamisligil, "Inflammation and Metabolic Disorders", Nature, vol. 444, No. 7121, Dec. 14, 2006, pp. 860-867.
Hu et al., "Corrigendum to "FAT1 Prevents Epithelial Mesenchymal Transition (EMT) via MAPK/ERK Signaling Pathway in Esophageal Squamous Cell Cancer"", Cancer Letters, vol. 494, 2020, pp. 1-2.
Hu et al., "FAT1 Prevents Epithelial Mesenchymal Transition (EMT) via MAPK/ERK Signaling Pathway in Esophageal Squamous Cell Cancer", Cancer Letters, vol. 397, 2017, pp. 83-93.
Ibrahim et al., "Non-alcoholic Steatohepatitis Pathogenesis: Sublethal Hepatocyte Injury as a Driver of Liver Inflammation", Gut, vol. 67, No. 5, May 2018, pp. 963-972.
Iyengar et al., "Obesity and Cancer: Local and Systemic Mechanisms", Annual Review of Medicine, vol. 66, 2015, pp. 297-309.
Iyer et al., "Animal Models Correlating Immune Cells for the Development of NAFLD/NASH", Journal of Clinical and Experimental Hepatology, vol. 5, No. 3, Sep. 2015, pp. 239-245.
Jiao et al., "Low-Fat Dietary Pattern and Pancreatic Cancer Risk in the Women's Health Initiative Dietary Modification Randomized Controlled Trial", Journal of the National Cancer Institute, vol. 110, 2018, pp. 49-56.
Kapoor et al., "Seesaw of Matrix Metalloproteinases (MMPs)", Journal of Cancer Research and Therapeutics, vol. 12, 2016, pp. 28-35.
Koeppel et al., "Role of Glutathione in Hepatic Bile Formation During Reperfusion After Cold Ischemia of the Rat Liver", Journal of Hepatology, vol. 28, No. 5, May 1998, pp. 812-819.
Korkmaz et al., "Neutrophil Elastase, Proteinase 3, and Cathepsin G as Therapeutic Targets in Human Diseases", Pharmacological Reviews, vol. 62, 2010, pp. 726-759.
Kretz et al., "Should We Keep Walking along the Trail for Pancreatic Cancer Treatment? Revisiting TNF-Related Apoptosis-Inducing Ligand for Anticancer Therapy", Cancers (Basel), vol. 10, 2018, pp. 1-27.
Lampel et al., "Acute Interstitial Pancreatitis in the Rat Induced by Excessive Doses of a Pancreatic Secretagogue", Virchows Archiv A Pathological Anatomy and Histology, vol. 73, No. 2, Mar. 11, 1977, pp. 97-117.
Lashinger et al., "Dietary Energy Balance Modulation of Kras- and Ink4a/Arf+/− Driven Pancreatic Cancer: The Role of Insulin-Like Growth Factor-I", Cancer Prevention Research (Phila), vol. 6, 2013, pp. 1046-1055.

(56) References Cited

OTHER PUBLICATIONS

Lau et al., "Animal Models of Non-alcoholic Fatty Liver Disease: Current Perspectives and Recent Advances", The Journal of Pathology, vol. 241, No. 1, Jan. 2017, pp. 36-44.
Lehv et al., "Pancreatic Acinar Cell Regeneration IV Regeneration After Resection", The American Journal of Pathology, vol. 53, 1968, pp. 513-535.
Lerch et al., "Models of Acute and Chronic Pancreatitis", Gastroenterology, vol. 144, 2013, pp. 1180-1193.
Liou et al., "The G-Protein-Coupled Receptor GPR40 Directly Mediates Long-Chain Fatty Acid-Induced Secretion of Cholecystokinin", Gastroenterology, vol. 140, 2011, pp. 903-912.
Liu et al., "The Role of n-3 Polyunsaturated Fatty Acids in the Prevention and Treatment of Breast Cancer", Nutrients, vol. 6, 2014, pp. 5184-5223.
Lo et al., "Cholecystokinin Knockout Mice are Resistant to High-Fat Diet Induced Obesity", Gastroenterology, vol. 138, 2010, pp. 1997-2005.
Lo et al., "Tumor-Promoting Desmoplasia Is Disrupted by Depleting FAP Expressing Stromal Cells", Cancer Research, vol. 75, 2015, pp. 2800-2810.
Lowenfels et al., "Epidemiology and Risk Factors for Pancreatic Cancer", Best Practice & Research: Clinical Gastroenterology, vol. 20, 2006, pp. 197-209.
Mainz et al., "Hormonal Control of Pancreatic Growth", Journal of Clinical Investigation, vol. 52, 1973, pp. 2300-2304.
Matters et al., "Cholecystokinin Mediates Progression and Metastasis of Pancreatic Cancer Associated with Dietary Fat", Digestive Diseases and Sciences, vol. 59, No. 6, Jun. 2014, pp. 1180-1191.
McLaughlin et al., "Fatty Acid Chain Length Determines Cholecystokinin Secretion and Effect on Human Gastric Motility", Gastroenterology, vol. 116, 1999, pp. 46-53.
McLaughlin et al., "Fatty Acids Stimulate Cholecystokinin Secretion via an Acyl Chain Length-Specific, Ca2+-Dependent Mechanism in the Enteroendocrine Cell Line STC-1", Journal of Molecular Signaling, vol. 513, 1998, pp. 11-18.
McWilliams et al., "Coexpression of Gastrin and Gastrin Receptors (CCK-B and Delta CCK-B) in Gastrointestinal Tumour Cell Lines", Gut, vol. 42, No. 6, Jun. 1998, pp. 795-798.
Miederer et al., "Efficient Treatment of Gastric Ulcer with Proglumide (Milid) in Outpatients (Double Blind Trial)", Acta Hepato-Gastroenterol (Stuttg), vol. 26, Aug. 1979, 6 pages.
Mishra et al., "Glycogen Synthase Kinase-3beta Regulates Snail and Beta-Catenin During Gastrin-Induced Migration of Gastric Cancer Cells", Journal of Molecular Signaling, vol. 5, No. 9, 2010, pp. 1-10.
Mittal et al., "Hepatocellular Carcinoma in the Absence of Cirrhosis in United States Veterans is Associated With Nonalcoholic Fatty Liver Disease", Clinical Gastroenterology and Hepatology, vol. 14, No. 1, Jan. 2016, pp. 124-131.
Moran, "Gut Peptides in the Control of Food Intake", International Journal of Obesity, vol. 33, No. 1, Apr. 2009, pp. S7-S10.
Moran et al., "Potent and Sustained Satiety Actions of a Cholecystokinin Octapeptide Analogue", The American Journal of Clinical Nutrition, vol. 55, 1992, pp. 286S-290S.
Mulders et al., "Microbiota in Obesity: Interactions with Enteroendocrine, Immune and Central Nervous Systems", Obesity Reviews, 2018, pp. 1-17.
Nadella et al., "Dietary Fat Stimulates Pancreatic Cancer Growth and Promotes Fibrosis of the Tumor Microenvironment Through the Cholecystokinin Receptor", American Journal of Physiology-Gastrointestinal and Liver Physiology, vol. 315, No. 5, Nov. 1, 2018, pp. G699-G712.
Nywening et al., "Targeting Tumour-Associated Macrophages with CCR2 Inhibition in Combination With FOLFIRINOX in Patients With Borderline Resectable and Locally Advanced Pancreatic Cancer: A Single-centre, Open-label, Dose-finding, Non-randomised, Phase 1b Trial", The Lancet Oncology, vol. 17, No. 5, May 2016, pp. 1-12.

Ochoa-Callejero et al., "Maraviroc, a CCR5 Antagonist, Prevents Development of Hepatocellular Carcinoma in a Mouse Model", PLoS One, vol. 8, No. 1, 2013, 13 pages.
Oseini et al., "Therapies in Non-Alcoholic Steatohepatitis (NASH)", Liver International, vol. 37, Supplement 1, Jan. 2017, pp. 97-103.
Park et al., "Prognostic Factors for Risk Stratification of Patients with Recurrent or Metastatic Pancreatic Adenocarcinoma Who Were Treated with Gemcitabine-Based Chemotherapy", Cancer Research and Treatment, vol. 48, 2016, pp. 1264-1273.
Passman et al., "A Modified Choline-deficient, Ethionine-supplemented Diet Reduces Morbidity and Retains a Liver Progenitor Cell Response in Mice", Disease Models & Mechanisms, vol. 8, No. 12, Dec. 2015, pp. 1635-1641.
Patel et al., "Obesity, Recreational Physical Activity, and Risk of Pancreatic Cancer in a Large U.S. Cohort", Cancer Epidemiology, Biomarkers & Prevention, vol. 14, 2005, pp. 459-466.
Pauletzki et al., "Inhibition of Gallbladder Emptying Decreases Cholesterol Saturation in Bile in the Richardson Ground Squirrel", Hepatology, vol. 22, No. 1, Jul. 1995, pp. 325-331.
Application No. PCT/US2019/059833, International Preliminary Report on Patentability, Mailed on May 20, 2021, 7 pages.
Application No. PCT/US2019/059833, International Search Report and Written Opinion, Mailed on Jan. 27, 2020, 9 pages.
Philip et al., "A High-Fat Diet Activates Oncogenic Kras and COX2 to Induce Development of Pancreatic Ductal Adenocarcinoma in Mice", Gastroenterology, vol. 145, 2013, pp. 1-22.
Pisani, "Hyper-Insulinaemia and Cancer, Meta-Analyses of Epidemiological Studies", Archives of Physiology and Biochemistry, vol. 114, 2008, pp. 63-70.
Reid et al., "Murine Models Provide Insight to the Development of Non-alcoholic Fatty Liver Disease", Nutrition Research Reviews, vol. 28, No. 2, Dec. 2018, pp. 133-142.
Rhim et al., "Stromal Elements Act to Restrain, Rather Than Support, Pancreatic Ductal Adenocarcinoma", Cancer Cell, vol. 25, 2014, pp. 735-747.
Ridlon et al., "Bile Acids and the Gut Microbiome", Current Opinion in Gastroenterology, vol. 30, No. 3, May 2014, pp. 332-338.
Roberts et al., "Biological Mechanisms Linking Obesity and Cancer Risk: New Perspectives", Annual Review of Medicine, vol. 61, 2010, pp. 301-316.
Roberts et al., "Western Diet-induced Hepatic Steatosis and Alterations in the Liver Transcriptome in Adult Brown—Norway Rats", BMC Gastroenterology, vol. 15, No. 151, Oct. 30, 2015, 14 pages.
Roebuck et al., "Effects of Dietary Fats and Soybean Protein on Azaserine-Induced Pancreatic Carcinogenesis and Plasma Cholecystokinin in the Rat", Cancer Research, vol. 47, 1987, pp. 1333-1338.
Roy et al., "Assessment of Cholecystokinin 2 Receptor (CCK2R) in Neoplastic tissue", Oncotarget, vol. 7, No. 12, Mar. 22, 2016, pp. 14605-14615.
Sanyal et al., "Pioglitazone, Vitamin E, or Placebo for Nonalcoholic Steatohepatitis", The New England Journal of Medicine, vol. 362, No. 18, May 6, 2010, pp. 1675-1685.
Shi et al., "miR-148a is Associated with Obesity and Modulates Adipocyte Differentiation of Mesenchymal Stem Cells through Wnt Signaling", Scientific Reports, vol. 5, No. 9930, 2015, pp. 1-11.
Shiratori et al., "Clinical Evaluation of Oral Administration of a Cholecystokinin-A Receptor Antagonist (Loxiglumide) to Patients with Acute, Painful Attacks of Chronic Pancreatitis: A Multicenter Dose-Response Study in Japan", Pancreas, vol. 25, 2002, pp. e1-e5.
Singh et al., "Novel Gastrin Receptors Mediate Mitogenic Effects of Gastrin and Processing Intermediates of Gastrin on Swiss 3T3 Fibroblasts. Absence of Detectable Cholecystokinin (CCK)-A and CCK-B Receptors", Journal of Biological Chemistry, vol. 270, No. 15, Apr. 14, 1995, pp. 8429-8438.
Singh et al., "Role of Gastrin and Gastrin Receptors on the Growth of a Transplantable Mouse Colon Carcinoma (MC-26) in BALB/c Mice", Cancer Research, vol. 46, No. 4, Part 1, Apr. 1986, pp. 1612-1616.
Smith et al., "Characterization of CCK-B/Gastrin-like Receptors in Human Gastric Carcinoma", International Journal of Oncology, vol. 12, No. 2, Feb. 1998, pp. 411-419.

(56) References Cited

OTHER PUBLICATIONS

Smith et al., "Characterization of the CCK-B/Gastrin-like Receptor in Human Colon Cancer", American Journal of Physiology, vol. 271, No. 3, Part 2, Sep. 1996, pp. R797-R805.

Smith et al., "Characterization of the CCK-C (Cancer) Receptor in Human Pancreatic Cancer", International Journal of Molecular Medicine, vol. 10, No. 6, Dec. 2002, pp. 689-694.

Smith et al., "Cholecystokinin and Pancreatic Cancer: The Chicken or The Egg?", American Journal of Physiology Gastrointestinal and Liver Physiology, vol. 306, No. 2, Jan. 15, 2014, pp. G91-G101.

Smith et al., "Cholecystokinin Receptor Antagonist Alters Pancreatic Cancer Microenvironment and Increases Efficacy of Immune Checkpoint Antibody Therapy in Mice", Cancer Immunology, Immunotherapy, 2017, pp. 1-13.

Smith et al., "Cholecystokinin Receptor Antagonist Halts Progression of Pancreatic Cancer Precursor Lesions and Fibrosis in Mice", Pancreas, vol. 43, No. 7, Oct. 2014, pp. 1050-1059.

Smith et al., "Gastrin and Gastric Cancer", Cellular and Molecular Gastroenterology and Hepatology, vol. 4, No., 1, Mar. 14, 2017, pp. 75-83.

Smith et al., "Identification and Characterization of CCK-B/Gastrin Receptors in Human Pancreatic Cancer Cell Lines", American Journal of Physiology, vol. 266, vol. 1, Part 2, Jan. 1994, pp. R277-R283.

Smith et al., "The Role of Gastrin and CCK Receptors in Pancreatic Cancer and other Malignancies", International Journal of Biological Sciences, vol. 12, No. 3, Jan. 28, 2016, pp. 283-291.

Solomon et al., "Cell Site and Time Course of DNA Synthesis in Pancreas After Caerulein and Secretin", American Journal of Physiology, vol. 245, Jul. 1983, pp. G99-G105.

Solomon , "Control of Exocrine Pancreatic Secretion", Physiology of the Gastrointestinal Tract, Third Edition, vol. 2, 1994, 33 pages.

Solomon et al., "Interaction of Caerulein and Secretin on Pancreatic Size and Composition in Rat", American Journal of Physiology, vol. 235, Dec. 1978, pp. E714-E719.

Steinert et al., "Ghrelin, CCK, GLP-1, and PYY(3-36): Secretory Controls and Physiological Roles in Eating and Glycemia in Health, Obesity, and After RYGB", Physiological Reviews, vol. 97, 2017, pp. 411-463.

Strouch et al., "A High Omega-3 Fatty Acid Diet Mitigates Murine Pancreatic Precancer Development", Journal of Surgical Research, vol. 165, 2011, pp. 75-81.

Sztefko et al., "CCK-receptor Antagonists Proglumide and Loxiglumide Stimulate Bile Flow and Biliary Glutathione Excretion", Digestive Diseases and Sciences, vol. 39, No. 3, Sep. 1994, pp. 1974-1980.

Thiebaut et al., "Dietary Fatty Acids and Pancreatic Cancer in the NIH-AARP Diet and Health Study", Journal of the National Cancer Institute, vol. 101, Jul. 15, 2009, pp. 1001-1011.

Tong et al., "Eating Disorders and Gastrointestinal Peptides", Current Opinion in Endocrinology, Diabetes and Obesity, vol. 18, 2011, pp. 42-49.

Tzeng et al., "The Ethanol Extract from Lonicera japonica Thunb. Regresses Nonalcoholic Steatohepatitis in a Methionine- and Choline-Deficient Diet-Fed Animal Model", Nutrients, vol. 7, No. 10, Oct. 21, 2015, pp. 8670-8684.

Varro et al., "Increased Gastric Expression of MMP-7 in Hypergastrinemia and Significance for Epithelial-Mesenchymal Signaling", The American Journal of Physiology: Gastrointestinal and Liver Physiology, vol. 292, 2007, pp. G1133-G1140.

Wang et al., "Role of Tumor Microenvironment in Tumorigenesis", Journal of Cancer, vol. 8, 2017, pp. 761-773.

Wank et al., "Brain and Gastrointestinal Cholecystokinin Receptor Family: Structure and Functional Expression", Proceedings of the National Academy of Sciences, vol. 89, No., 18, Sep. 15, 1992, pp. 8691-8695.

Wank et al., "Cholecystokinin Receptor Family. Molecular Cloning, Structure, and Functional Expression in Rat, Guinea Pig, and Human", Annals of the New York Academy of Sciences, vol. 713, Mar. 1994, pp. 49-66.

Weinberg et al., "Cholecystokinin A and B Receptors are Differentially Expressed in Normal Pancreas and Pancreatic Adenocarcinoma", Journal of Clinical Investigation, vol. 100, No. 3, Aug. 1, 1997, pp. 597-603.

Willier et al., "Lysophosphatidic Acid (LPA) Signalling in Cell Migration and Cancer Invasion: A Focussed Review and Analysis of LPA Receptor Gene Expression on the Basis of More Than 1700 Cancer Microarrays", Biology of the Cell, vol. 105, 2013, pp. 317-333.

Wu et al., "Profiling Peripheral microRNAs in Obesity and Type 2 Diabetes Mellitus", APMIS, vol. 123, 2015, pp. 1-6.

Xu et al., "Anti-Cancer Activities of ω-6 Polyunsaturated Fatty Acids", Biomedical Journal, vol. 37, No. 3, 2014, pp. 112-119.

Xu et al., "Systematic Review and Meta-Analysis on the Association Between IL-1B Polymorphisms and Cancer Risk", PLoS One, vol. 8, No. 5, 2013, pp. e63654-e63654.

Yadav et al., "The Epidemiology of Pancreatitis and Pancreatic Cancer", Gastroenterology, vol. 144, 2013, pp. 1252-1261.

Yao et al., "Saturated, Monounsaturated and Polyunsaturated Fatty Acids Intake and Risk of Pancreatic Cancer: Evidence from Observational Studies", Public Library of Science One, vol. 10, Jun. 25, 2015, pp. 1-14.

Yu et al., "Four Types of Fatty Acids Exert Differential Impact on Pancreatic Cancer Growth", Cancer Letters, vol. 360, 2015, pp. 187-194.

Zhang et al., "Cholecystokinin Octapeptide Regulates Lipopolysaccharide-Activated B Cells Co-Stimulatory Molecule Expression and Cytokines Production in Vitro", Immunopharmacology and Immunotoxicology, vol. 33, No. 1, Mar. 2011, pp. 157-163.

Zhang et al., "Cholecystokinin Octapeptide Regulates the Differentiation and Effector Cytokine Production of CD4 T Cells In Vitro", International Immunopharmacology, vol. 20, No. 2, Jun. 2014, pp. 307-315.

Zhao et al., "Obesity and Genetics Regulate microRNAs in Islets, Liver, and Adipose of Diabetic Mice", Mammalian Genome, vol. 20, 2009, pp. 476-485.

Zheng et al., "Role of Immune Cells and Immune-Based Therapies in Pancreatitis and Pancreatic Ductal Adenocarcinoma", Gastroenterology, vol. 144, 2013, pp. 1230-1240.

Zoller et al., "Nonalcoholic Fatty Liver Disease and Hepatocellular Carcinoma", Metabolism, vol. 65, No. 8, Aug. 2016, pp. 1151-1160.

Zucker et al., "Effects of the CCK Receptor Antagonist L364,718 on Pancreatic Growth in Adult and Developing Animals", American Journal of Physiology, vol. 257, 1989, pp. G511-G516.

Zyromski et al., "Obesity Potentiates the Growth and Dissemination of Pancreatic Cancer", Surgery, vol. 146, 2009, pp. 258-263.

EP19883232.1 , "Extended European Search Report", Jul. 11, 2022, 6 pages.

Tucker et al., "A Cholecystokinin Receptor Antagonist Halts Nonalcoholic Steatohepatitis and Prevents Hepatocellular Carcinoma", Digestive Diseases and Sciences, vol. 65, No., 1, Jul. 11, 2019, pp. 189-203.

AU2019376630, "First Examination Report", Jul. 18, 2024, 2 pages.

Setnikar I et al.: "Loxiglumide protects against experimental pancreatitis", Oct. 1, 1987 (Oct. 1, 1987), pp. 1-1, XP093244150, Retrieved from the Internet: URL:https://pubmed.ncbi.nlm.nih.gov/3435590/.

Anonymous Chun-Ping et al: "Effects of Gastrin and Its Receptor Antagonist Proglumide on the Growth of Hepatocellular Carcinoma Cell Lines", World Chinese Journal of Digestology, vol. 16, No. 15, May 28, 2008 (May 28, 2008), p. 1677, XP093244088, ISSN: 2219-2859, DOI: 10.11569/wcjd.v16.i15.1677 Retrieved from the Internet: URL:https://www.wjgnet.com/1009-3079/full/v16/i15/1677.htm.

Communication Pursuant to Article 94(3) EPC issued on Feb. 3, 2025, in EP Application No. 19883232.1.

\* cited by examiner

Week-12 CDE/Reg 40X

Week-12 CDE/Proglumide 40X

Week-18, CDE/Reg 10X
Dysplastic Nodule

Week-18, CDE/Reg 4X
Hepatocellular Cancer

E. Control/Reg

F. Control/Proglumide

G Histology Scores from Livers of Mice on Control Diet

| GROUP | Inflammation | Fibrosis | Steatosis | Ballooning | Dysplasia/Cancer |
|---|---|---|---|---|---|
| Control Reg | 0 | | 1.8±0.2 | 0 | 0 |
| Control-Proglumide | 0 | | 1.8±0. | 0 | 0 |

FIGS. 5A–5G

TREATING NON-ALCOHOLIC STEATOHEPATITIS WITH CCK INHIBITORS

This application claims priority to U.S. Provisional Application No. 62/756,384, filed Nov. 6, 2018, which is hereby incorporated in its entirety by this reference.

BACKGROUND

Non-alcoholic steatohepatitis (NASH) is a common inflammatory liver condition that may lead to cirrhosis and hepatocellular cancer (HCC). NASH is one of the leading causes of liver-related morbidities and mortalities and its occurrence has increased sharply since the beginning of the $21^{st}$ century. Obesity and high fat diets are considered primary drivers of this epidemic in both industrialized and developing countries. Thus, the prevalence of NASH is increasing as more people adopt a higher fat Western diet. With the exception of weight loss and vitamin E therapy, few treatments are effective in treating NASH.

SUMMARY

Provided herein are methods for treating NASH in a subject. The methods comprise administering a cholecystokinin (CCK) receptor inhibitor to a subject having NASH. Administration of the CCK receptor inhibitor to the subject can decrease liver fibrosis and inflammation and/or can prevent HCC in the subject. Also provided are methods for treating hepatic fibrosis in a subject.

BRIEF DESCRIPTION OF THE FIGURES

FIG. 1 is a flowchart of a two-part study design to treat or prevent NASH. In the prevention study, mice were treated with the choline-deficient, ethionine-supplemented (CDE) diet with untreated or regular drinking water (CDE/Reg Diet) to induce NASH and some mice received the CDE diet and a CCK receptor antagonist, proglumide, supplemented drinking water (CDE/Prog) to determine if CCK receptor antagonism could prevent NASH. The differences in these two cohorts were assessed at weeks 12 and 18. In the reversal study, after N=30 mice had received the CDE diet and untreated water for 12 weeks and had established NASH, half of these mice were then treated with proglumide while continuing on the CDE diet. Control mice received the same Western diet with the same components of saturated fat, protein and carbohydrates as the CDE-treated mice, but with choline added.

FIG. 2A shows the final body weights at week 18 for each treatment group. Mice on the control diet gained more weight than all of the mice on the CDE diet. Mice on the CDE/Reg diet had the lowest body weights at the conclusion of the study and this was significantly lower than the mice on the CDE diet that received proglumide for 18 weeks. The weight was also significantly lower in mice that received the CDE/Reg diet for 12 weeks and then received proglumide in their drinking water for weeks 13-18; FIG. 2B shows the results of food intake over 12 weeks. Mice on the CDE/Reg diet ate less food than the other mice. The response to proglumide in the CDE/Prog-treated mice was not due to weight loss. This indicates that CCK-receptor blockade is effective in NASH independent of weight loss. Since the mice on the CDE/Prog treatment actually ate more food than the CDE/regular mice, one would expect them to have more advanced liver disease, but instead they had less.

FIG. 3A shows that serum AST levels were significantly increased in CDE/Reg mice compared to mice on the control Western diet high fat diet chow and given untreated (Reg) or proglumide treated water. Aspartate aminotransferase (AST) levels were at or near normal levels in mice on the CDE diet that received proglumide starting on day 0 in their drinking water (Prevention). AST levels also significantly decreased in mice that were fed the CDE/Reg food/water for 12 weeks the then switched to CDE/Prog for 6 weeks (Recovery). FIG. 3B shows that serum bilirubin was significantly increased in mice in the CDE/Reg group at weeks 12 and 18 compared to mice on the control high fat diet. Proglumide therapy prevented bilirubin level increases in mice on the CDE diet and proglumide also decreased bilirubin in mice switched at week 12 from untreated water to proglumide water. FIG. 3C shows that alkaline phosphatase blood levels were elevated in mice fed the CDE diet compared to the control diet, but proglumide did not decrease alkaline phosphatase, because this represented drug-induced liver injury from the ethionine. FIG. 3D shows that alanine aminotransferase (ALT) serum levels were increased in mice on the CDE diet compared to the control diet. Proglumide treated water was able to prevent this increase only after 18 weeks, not at week 12. Although mice that received CDE/Reg for 12 weeks and then CDE/Prog for the last 6 weeks (Recovery) had lower ALT values compared to those that were on the CDE/Reg for 18 full weeks, this difference was not significant.

FIG. 4A and FIG. 4B show histologic scores at week 12 and week 18, respectively, of the animals from the study outlined in FIG. 1. Proglumide therapy prevented all 3 histologic parameters (inflammation, fibrosis and steatosis), while on the high fat CDE diet at both week 12 (FIG. 4A) and 18 (FIG. 4B). When histologic NASH was confirmed at week 12 on the CDE/Reg diet, proglumide intervention was able to decrease inflammation and fibrosis when given for 6 subsequent weeks while continuing the CDE high fat diet (Recovery). However, the score for steatosis was not significantly changed in the recovery treatment group.

FIG. 5A is a Masson's Trichrome stain of week-12 livers that revealed steatosis, balloon degeneration (arrows), and fibrosis in mice on the CDE diet/Regular water. FIG. 5B shows that the histologic features of NASH were significantly decreased in week-12 livers of mice on the CDE diet treated with the CCK receptor antagonist proglumide in the drinking water. FIG. 5C shows a dysplastic nodule in a liver of a mouse at week-18 on the CDE/Reg diet. FIG. 5D shows that hepatoccellular carcinoma was only found in mice on the CDE/Reg diet at week 18 and in none of the proglumide treated mice. FIG. 5E shows liver histology from a representative mouse on the high fat control/Reg diet at week 18. This mouse liver shows macrosteatosis, but no evidence of NASH (i.e., no inflammation, fibrosis or balloon degeneration). FIG. 5F shows that liver histology from a control/proglumide-treated mouse also shows non-alcoholic fatty liver disease (NAFLD) with macrosteatosis but no evidence of NASH. FIG. 5G provides the mean±SEM for histologic scores of the control mice for inflammation, fibrosis, steatosis, ballooning and cancer. The only histologic abnormality identified in these control mice was steatosis.

DETAILED DESCRIPTION

NASH is a metabolic syndrome associated with chronic inflammation and alterations in tissue cytokines in the liver. This chronic inflammatory state, characteristic of NASH, induces histologic evidence of hepatocyte injury with balloon degeneration, fibrosis, and possibly HCC. The fastest growing cause of cancer-related death is HCC, and with the current obesity epidemic and improved therapy for hepatitis C, NASH-related HCC will soon surpass that of viral hepatitis as the primary indication for orthotopic liver transplantation.

Current therapies for treating NAFLD and NASH have had modest success. Weight reduction and dietary management have been treatment mainstays, but 10% or more of a patient's body weight must be lost for inflammation to decrease and fibrosis to improve. Pharmacological treatments, such as statins, have been only moderately successful if hyperlipidemia is contributing to NASH. The PIVENS trial using Vitamin E and pioglitazone showed the most promise in treating NASH; however, neither compound statistically reversed fibrosis; furthermore, neither is recommended for those with diabetes mellitus.

Animal models to study NASH and HCC have been developed. A special diet that is deficient in choline and supplemented with ethionine (CDE diet) has been shown to induce more rapid hepatic fibrosis and to result in histologic characteristics similar to NASH. A slightly modified version of the diet with 75% (rather than 100%) CDE diet is less toxic and results in HCC.

Human subjects that consume a high saturated fat diet are found to have elevated CCK levels. It was also reported that CCK blood levels were 10-fold higher in mice on the high fat (TestDiet, St. Louis MO, catalog #58Y2) compared to mice on standard chow and that this high fat diet induced NAFLD. CCK exerts its effects through a G-protein coupled receptor called the CCK-receptor. Two classic CCK receptors, the CCK-A (CCK-1) and CCK-B (CCK-2) receptors have been identified. CCK receptors have been identified in precancerous pancreatic intraepithelial neoplasia (PanIN) lesions. CCK receptors have also been identified on fibroblasts or stellate cells and blockade of these receptors by CCK receptor antagonists prevents fibrosis or collagen deposit. As shown herein, CCK receptor blockade prevented dietary-induced NASH and also reversed biochemical and histologic alterations of NASH in a mouse model of steatohepatitis. Further, CCK receptor blockade with a CCK receptor inhibitor prevented the development of HCC.

Provided herein is a method for treating NASH in a subject, comprising administering to a subject having NASH an effective amount of a CCK receptor inhibitor. In any of the methods provided herein, administration of a CCK receptor inhibitor can decrease inflammation in the subject with NASH. More particularly, administration of a CCK receptor inhibitor can decrease inflammation. In any of the methods provided herein, administration of a CCK receptor inhibitor can prevent the development or progression of cirrhosis in a subject having NASH and/or decrease fibrosis, for example, reverse established fibrosis in a subject. Optionally, administration of a CCK receptor inhibitor can decrease inflammation in a subject. In any of the methods provided herein, administration of a CCK receptor inhibitor can prevent the development of progression of HCC in a subject having NASH. In any of the methods provided herein, a CCK receptor antagonist can also reverse established fibrosis of the liver in a subject.

Also provided is a method of treating hepatic or liver fibrosis comprising administering to a subject having hepatic fibrosis a CCK receptor inhibitor or antagonist that inhibits one or more CCK receptors selected from the group consisting of a CCK-A (CCK-1) receptor, a CCK-B (CCK-2 or gastrin) receptor and a CCK-C receptor. Optionally, the hepatic fibrosis is caused by alcohol abuse, a viral infection (for example, hepatitis B or hepatitis C), a biliary obstruction, iron overload, NASH, or NAFL, to a name a few. Optionally, the CCK receptor inhibitor that treats hepatic fibrosis is proglumide.

In any of the methods provided herein, the CCK receptor inhibitor or antagonist can be a CCK receptor inhibitor or antagonist that inhibits one or more CCK receptors selected from the group consisting of a CCK-A (CCK-1) receptor, a CCK-B (CCK-2 or gastrin) receptor and a CCK-C receptor. In any of the methods provided herein, the CCK receptor antagonist can decrease fibrosis in the subject, for example, liver fibrosis. Optionally, administration of a CCK receptor antagonist decreases fibrosis, for example, NASH-associated fibrosis, in the subject. Optionally, administration of a CCK receptor antagonist decreases fibrosis associated with viral hepatitis (hepatitis B, hepatitis C and HIV fibrosis), alcoholic hepatitis, cirrhosis, autoimmune hepatitis, primary biliary cholangitis or sclerosing cholangitis. Optionally, administration of a CCK receptor antagonist decreases a macrophage inflammatory response associated with fibrosis, for example, NASH-associated fibrosis, in the subject.

As used throughout, fibrosis, refers to a process resulting in excess deposition of extracellular matrix components, for example, collagen. See, for example, Cox and Erler "Molecular Pathways: Connecting Fibrosis and Solid Tumor Metastasis," *Clin Cancer Res;* 20 (14); 3637-43, hereby incorporated in its entirety by this reference. In any of the methods provided herein, a decrease in fibrosis can be a decrease of about 10, 20, 30, 40, 50, 60, 70, 80, 90% or greater when compared to fibrosis in the subject prior to treatment with a CCK receptor antagonist or when compared to a control subject or control value.

In some examples, the CCK receptor inhibitor or antagonist inhibits the CCK-A receptor and the CCK-B receptor. For example, and not to be limiting, proglumide can be used to inhibit both the CCK-A receptor and the CCK-B receptor. In any of the methods provided herein, a CCK-A receptor antagonist, a CCK-B receptor antagonist, or an antagonist that inhibits both the CCK-A receptor and the CCK-B receptor (for example, proglumide) can be administered to the subject.

In some examples, the CCK receptor inhibitor or antagonist selectively or preferentially inhibits the CCK-A receptor, the CCK-B receptor or the CCK-C receptor (a variant of the CCK-B receptor). An example of a CCK receptor antagonist that selectively or preferentially inhibits the CCK-A receptor, is L364,718 (Devazepide). Other examples of antagonists that preferentially inhibit the CCK-A receptor include, but are not limited to Lorglumide, Loxiglumide, Dexloxiglumide, and Lintript (See Berna et al. *Curr. Top. Med. Chem.* 7 (12): 1211-1231 (2007)), hereby incorporated in its entirety by this reference). Examples of antagonists that preferentially inhibit the CCK-B receptor include, but are not limited to, Spiroglumide, Itriglumide, CI-988, L365, 260 and YF476 (See Berna et al.).

Any of the methods provided herein can further comprise administering a second therapeutic agent (in combination therapy) to the subject. In some methods, the second therapeutic agent is metformin, pioglitazone, vitamin E or a statin (for example, lovastatin, atorvastatin, simvastatin, pravastatin, rosuvastatin or fluvastatin). It is understood that two or more second therapeutic agents can be administered to the subject. Optionally, the CCK receptor and/or the second therapeutic agent can be administered at a dosage lower than the dosage administered to the subject when the CCK receptor inhibitor or second therapeutic agent is delivered as a monotherapy. Alternatively, the CCK receptor inhibitor can be administered in conjunction with other therapies for liver disease. For example, the composition can be administered to a subject at the same time, prior to, or after surgery, immunotherapy, transplant therapy or other pharmacotherapy.

In some methods, the CCK receptor inhibitor is administered in conjunction with a chemotherapeutic agent or immune checkpoint inhibitor (for example, an immune checkpoint antibody such as an anti-CTLA-4 antibody, an anti-PD-1 antibody or an anti-PD-L1 antibody) to prevent progression of HCC. The chemotherapeutic or immune checkpoint inhibitor can be administered prior to, concurrently with or subsequent to treatment with a CCK receptor inhibitor. Examples of chemotherapeutic agents include, but are not limited to, antineoplastic agents such as Acivicin; Aclarubicin; Acodazole Hydrochloride; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; 5-Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin C; Mitosper; Mitotane; Mitoxantrone; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safmgol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Other chemotherapeutic agents that can be used include, sorafenib, brivanib, sunitinib, linifanib, erlotinib, everolimus, ramucirumab, regorafenib, lenvatinib, cabozantinib, tivantinib, apatinib, to name a few. Examples of immune checkpoint inhibitors include, but are not limited to pembrolizumab, nivolumab, cemiplimab, durvalumab, atezolizumab, avelumab, and ipilimumab. Any of the methods provided herein for preventing HCC can optionally further include administering radiation therapy to the subject.

Any of the methods provided herein can further comprise weight loss and/or dietary modifications for the subject. For example, the subject can limit fat intake, replace saturated fats and trans fats with monounsaturated fats and polyunsatured fats, reduce sugar intake, avoid alcohol use, reduce non-skim dairy consumption and/or reduce sodium intake.

The methods provided herein can further comprise diagnosing the subject with NASH. For example, and not to be limiting, an MRI elastography, a liver biopsy, an ultrasound, Fibroscan, and/or a blood test to (for example, NASH Fibrosure®) assess liver function can be used to diagnose NASH. It is also understood that any of the methods provided herein can be used to treat a subject suspected of having NASH.

Treating or treatment of any disease or disorder refers to ameliorating a disease or disorder that exists in a subject. The term ameliorating refers to any therapeutically beneficial result in the treatment of a disease state, e.g., NASH, lessening in the severity or progression, promoting remission or durations of remission, or curing thereof. Thus, treating or treatment includes ameliorating at least one physical parameter or symptom. Treating or treatment includes modulating the disease or disorder, either physically (e.g., stabilization of a discernible symptom) or physiologically (e.g., stabilization of a physical parameter) or both. Treating or treatment includes delaying or preventing progression of NASH. It is understood that progression of NASH can result in fibrosis, cirrhosis and/or HCC. Therefore, treating NASH can also prevent the development or progression of fibrosis, cirrhosis and/or HCC. In the disclosed methods, treatment can refer to a 10%, 20%, 30%, 40%, 50%, 60%, 70%, 80%, 90%, or 100% reduction in the severity of an established disease or condition or symptom of the disease or condition. For example, a method for treating NASH is considered to be a treatment if there is a 10% reduction in one or more symptoms of the disorder (for example, inflammation, pain, swelling etc.), a decrease in fibrosis (for example, NASH-associated liver fibrosis), a reduction in the severity of NASH, the complete ablation of NASH, or a delay in the onset or worsening of one or more symptoms of NASH. In another example, a method for treating hepatic fibrosis, regardless of the cause of the hepatic fibrosis in the subject, is considered to be treatment if there is a 10% reduction in fibrosis in the subject. Thus, the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used throughout, by subject is meant an individual. Preferably, the subject is a mammal such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical formulations are contemplated herein.

As used herein, the term therapeutically effective amount or effective amount is defined as any amount necessary to produce a desired physiologic response, for example, treating a disease or disorder. A suitable dose of a CCK receptor antagonist described herein, which dose is capable of treating NASH in a subject, can depend on a variety of factors including whether it is used concomitantly with other therapeutic agents. Other factors affecting the dose administered to the subject include, e.g., the severity of NASH. Other factors can include medical issues or disorders concurrently or previously affecting the subject (for example, diabetes, high cholesterol, hypothyrodisim, etc.), the general health of the subject, the genetic disposition of the subject, diet, time of administration, rate of excretion, drug combination, age or size of the subject, and any other additional therapeutics that are administered to the subject. It should also be understood that a specific dosage and treatment regimen for any particular subject also depends upon the judgment of the treating medical practitioner. A therapeutically effective amount is also one in which any toxic or detrimental effects of the composition are outweighed by the therapeutically beneficial effects.

Exemplary dosage amounts for administration of a CCK receptor antagonist include doses from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 50 mg/kg of body weight of active compound per day, about 1 to about 40 mg/kg of body weight of active compound per day, about 1 to about 30 mg/kg of body weight of active compound per day, about 1 to about 30 mg/kg of body weight of active compound per day, about 30 mg/kg of body weight of active compound per day about 20 mg/kg of body weight of active compound per day, about 10 mg/kg of body weight of active compound per day, or about 5 mg/kg of body weight of active compound per day.

The dosage amounts for administration of a CCK receptor antagonist include doses from about 1 mg to 2000 mg of active compound per day, which may be administered in a single dose or in the form of individual divided doses, such as from 1 to 4 times per day. Alternatively, the dosage amount can be from about 100 mg to about 300 mg of active compound per day, about 200 mg to about 600 mg of active compound per day, about 200 mg to about 600 mg of active compound per day, about 200 mg to about 900 mg of active compound per day, about 300 mg to about 900 mg of body weight of active compound per day, about 300 mg to about 1200 mg of active compound per day, about 600 mg to about 1200 mg of active compound per day, about 300 mg to about 1600 mg of active compound per day, about 600 mg to about 1600 mg of active compound per day, about 300 mg to about 2000 mg of active compound per day, or about 600 mg to about 2000 mg of active compound per day. In some examples, about 300 mg, about 400 mg or about 500 mg of proglumide is administered 1, 2, 3 or 4 times a day. One of skill in the art would adjust the dosage as described below based on specific characteristics of the inhibitor and the subject receiving it.

Effective amounts and schedules for administering a CCK receptor antagonist can be determined empirically and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, unwanted cell death, and the like. Generally, the dosage will vary with the type of inhibitor, the species, age, body weight, general health, sex and diet of the subject, the mode and time of administration, rate of excretion, drug combination, and severity of the particular condition and can be determined by one of skill in the art. The dosage can be adjusted by the individual physician in the event of any contraindications. Dosages can vary, and can be administered in one or more dose administrations daily.

The CCK-R antagonists described herein can be provided in a pharmaceutical composition. These include, for example, a pharmaceutical composition comprising a therapeutically effective amount of one or more CCK-R antagonists and a pharmaceutical carrier.

Depending on the intended mode of administration, the pharmaceutical composition can be in the form of solid, semi-solid or liquid dosage forms, such as, for example, tablets, capsules suppositories, pills, capsules, powders, liquids, or suspensions, preferably in unit dosage form suitable for single administration of a precise dosage. The compositions will include a therapeutically effective amount of the agent described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected agent without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 22nd edition, Loyd V. Allen et al, editors, Pharmaceutical Press (2012).

Examples of physiologically acceptable carriers optionally include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, New Jersey), polyethylene glycol (PEG), and PLURONICS™ (BASF; Florham Park, NJ).

Compositions containing the agent(s) described herein suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof are admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

The compositions are administered in a number of ways depending on whether local or systemic treatment is desired and on the area to be treated. The compositions are administered via any of several routes of administration, including orally, parenterally, intravenously, intraperitoneally, intramuscularly, subcutaneously, intrarectally, intracavity or transdermally. Pharmaceutical compositions can also be delivered locally to the area in need of treatment (e.g., to the liver), for example by local application (e.g., during surgery) or local injection. Administration can also be achieved by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; and European Patent Nos. EP488401 and EP 430539. The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

Effective doses for any of the administration methods described herein can be extrapolated from dose-response curves derived from in vitro or animal model test systems.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Animal Models

All mouse studies were performed in an ethical fashion and approved by the Institutional Animal Care and Use Committee, protocol #2016-1193 for animal research by Georgetown University. Female C57BL/6 mice (body weight of >20 g) were obtained from Charles River Laboratory (Germantown, MD). Mice were housed with five per cage with filter-top cages and housing light cycled q12 hrs; on-off.

Diets

Mice were fed one of two custom high fat diets from MP Biomedicals, LLC (Solon, Ohio). The first group received a modified Choline Deficient Diet with 75% Ethionine supplemented diet (CDE) as previously described by Passman et al. "A modified choline-deficient, ethionine-supplemented diet reduces morbidity and retains a liver progenitor cell response in mice," *Dis Model Mech* 8:1635-1641 (2015). This modified diet has been shown to induce NASH and HCC. The control mice received the same diet with choline. Both diets contained casein as the major source of protein and lard (saturated fat) as the primary source of fat. The diet composition is shown in Table 1 and is very similar to the Western diet (Roberts et al. "Western diet-induced hepatic steatosis and alterations in the liver transcriptome in adult Brown-Norway rats," *BMC Gastroenterol.* 15:151 (2015)) where the diet consists of a high fat and high sugar and is often used in experimental animal diets to induce NAFLD. The food intake was measured by weighing food consumed to assure mice were eating equal amounts of food in each group, and animals ate ad libitum.

TABLE 1

Compositions of diets

|  | %/weight | % Kcal |
|---|---|---|
| Protein (Casein 50%) | 20 | 16.5 |
| Fat (Lard) Saturated 40% Unsaturated 60% | 20 | 37.2 |
| Carbs | 56 | 46.2 |
| minerals | 3.5 |  |
| fiber/other | 0.5 |  |

| Kcal per component of diet Components | Weight g |
|---|---|
| Vitamin tested Casein | 2000 |
| Alpha Protein | 2000 |
| *DL-Ethionine: | 100 |

TABLE 1-continued

Compositions of diets

| Sucrose | 11,200 |
|---|---|
| Lard | 4000 |
| AIN Mineral mix 76 | 700 |
| MP Vitamin Diet | With or without |
| Fortification Mixture | Choline |

*Ethionine added to choline deficient diet

Treatment

Some mice on both diets were treated with the CCK receptor antagonist proglumide (Tocris Bioscience, Bristol, UK) at a concentration of 0.1 mg/ml and the estimated amount ingested per mouse was 30 mg/kg/d that was previously shown to block the CCK receptor (Smith et al. "Cholecystokinin receptor antagonist halts progression of pancreatic cancer precursor lesions and fibrosis in mice," *Pancreas* 43:1050-1059 (2014)). Another cohort received untreated drinking water.

Study Design

Figure 1:
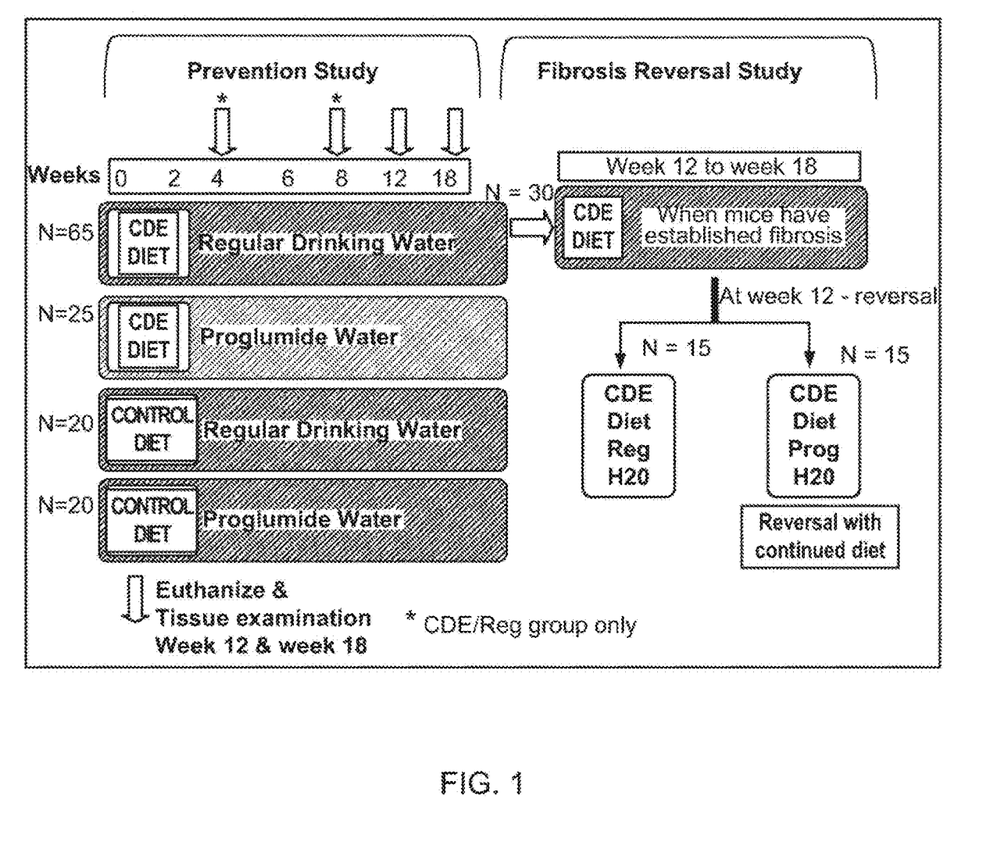

The study design included two different parts: a "prevention study" and a "reversal study" (FIG. 1). In the prevention study, the goal was to determine if treatment with proglumide could prevent NASH, fibrosis and HCC if started at the same time of the initiation of the high fat CDE diet. Initially mice were randomized into one of four treatment group (FIG. 1). Sixty-five mice received the 75%-CDE diet and untreated drinking water (CDE/Reg). Of these (N=5 each) mice were ethically euthanized and livers dissected and analyzed histologically to assess for evidence of NASH at weeks 4 and 8. When NASH was becoming apparent, mice were continued on this diet and some (N=10) were euthanized at week 12 and some (N=25) were euthanized at week 18. Five mice died in the CDE/Reg diet in the first 12 weeks.

A parallel cohort of mice (N=25) were also given the CDE diet but their drinking water was treated with the CCK-receptor antagonist proglumide. In this cohort, some (N=10) were euthanized, blood drawn, and liver examined histologically at week 12. The remainder (N=15) were euthanized and examined at week 18 to compare to the CDE/Reg group. Twenty mice each were treated with the control diet, and half (N=10) in this group received proglumide water and half received untreated drinking water. Half of the control mice were euthanized at the first time point of 12 weeks and the remainder was euthanized at the end of the experiment at 18 weeks.

The reversal study, took mice that had been on the CDE diet and untreated water (CDE/Reg) for 12 weeks (a time determined to result in the mice having NASH histologically and biochemical hepatitis). Mice were randomly allocated to one of two groups at 12 weeks. The first group (N=15) continued on the CDE diet and untreated water and the second group (N=15) also continued on the CDE diet but then received proglumide in the drinking water at the same concentration as the prevention study (0.1 mg/ml). The purpose of the reversal study was to see if proglumide could reverse any of the histologic and biochemical abnormalities of NASH from the 12-week CDE/regular water diet. The other group continued on the CDE diet with untreated drinking water. The animals in each group were weighed weekly. At the termination of the experiment the animal body weight and liver weight were recorded.

Biochemical Liver Transaminase Assessment

Subgroups of mice were ethically euthanized after $CO_2$ asphyxiation and cervical dislocation at one of 4 different time points: weeks 4, 8, 12, or 18. Blood was collected by pericardiac puncture and centrifuged. Serum was analyzed by VRL Laboratories (Gaithersburg, MD). The following liver tests were evaluated and the normal range for mouse is shown: Alkaline phosphatase (35-275 u/L); Alanine aminotransferase, ALT (17-129 u/L); Aspartate aminotransferase, AST (46-392 u/L); and total bilirubin (0-0.9 mg/dL).

Histologic Evaluation

The liver tissues were fixed in 4% paraformaldehyde, paraffin embedded, and 8 μm sections were cut. Mounted sections were stained with Hematoxylin & Eosin or Masson's trichrome. A Liver pathologist blinded to the treatments and time period scored tissues for inflammation, fibrosis, steatosis, and whether there was evidence of dysplastic nodules or cancer (Table 2). Histology was scored for grade of inflammation (0-3), fibrosis (0-4), steatosis (0-3), balloon degeneration (0-2) and dysplasia or cancer (0-2). For analysis, a NASH score was defined as the combination of the steatosis and the balloon degeneration score.

TABLE 2

Numeric scoring system used for histology.

| | Activity grade/ Inflammation | Fibrosis | Steatosis | Balloon degeneration | Dysplasia/ Cancer |
|---|---|---|---|---|---|
| Liver score: | None-0 | None -0 | <5% 0 | None- 0 | None -0 |
| | mild-1 | fibrosis without septa -1 | 5-33%-1 | Few -1 | Dysplastic nodules-1 |
| | moderate-2 | fibrosis with few septa -2 | 34-66%-2 | Many -2 | Cancer -2 |
| | severe-3 | Numerous septa no cirrhosis -3 Cirrhosis -4 | >66%-3 | | |

Statistical Analysis

Mean values for laboratory blood tests, animal body weights, and histology scores were calculated for each treatment group and compared to controls with paired-student-T analysis with Bonferroni correction if multiple comparisons to control were made.

Results

Animal and Food Weights

Figure 2A:
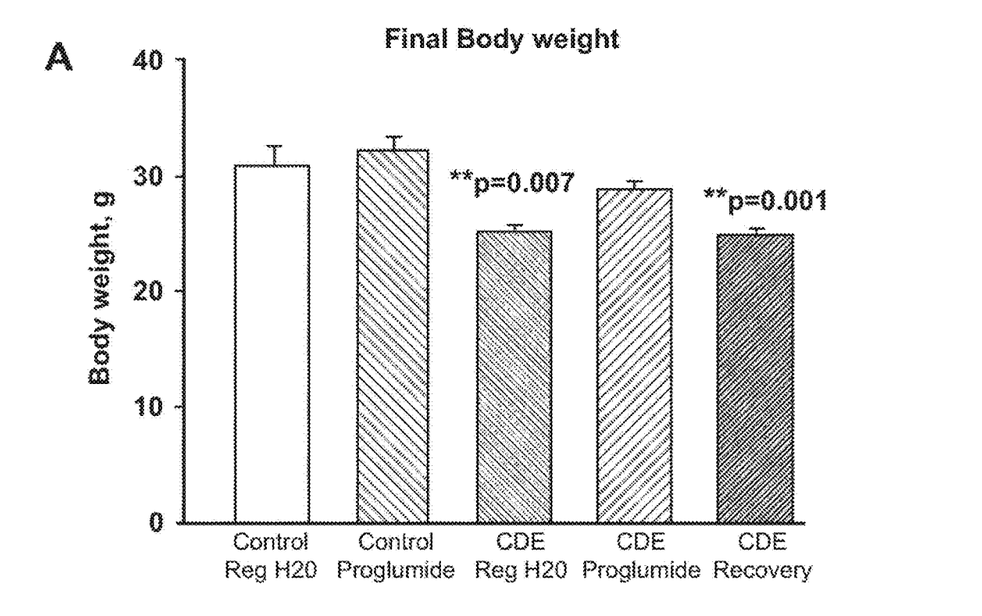
FIG. 2A and FIG. 2B show the effects of proglumide on body weight and food intake, respectively, after conducting the study outlined in FIG. 1.
Figure 2B:
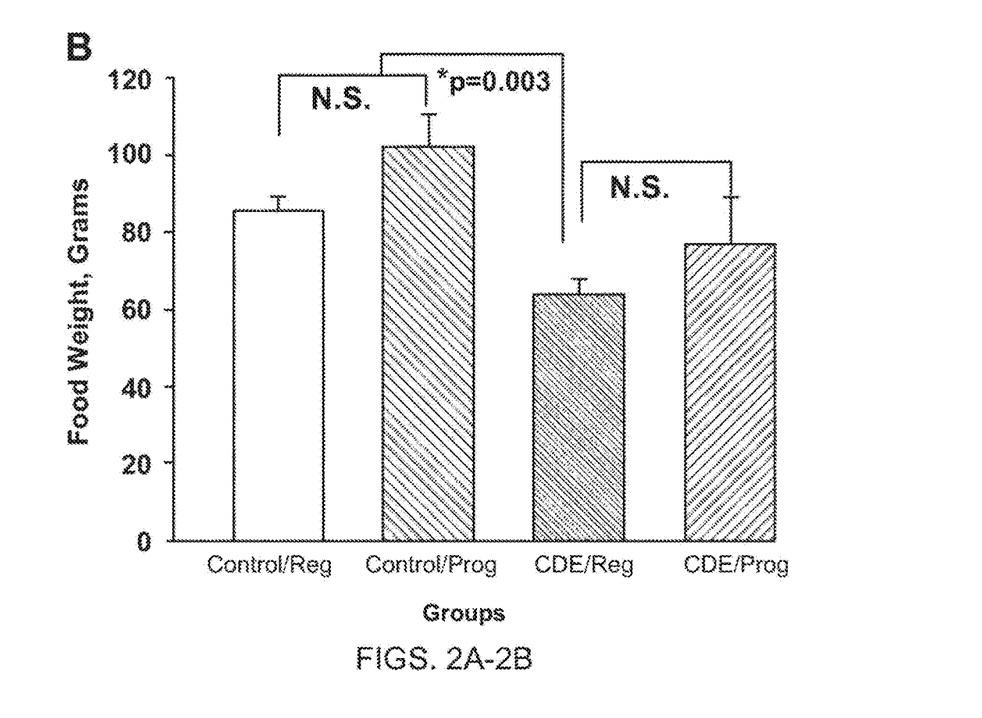
Figure 3A:
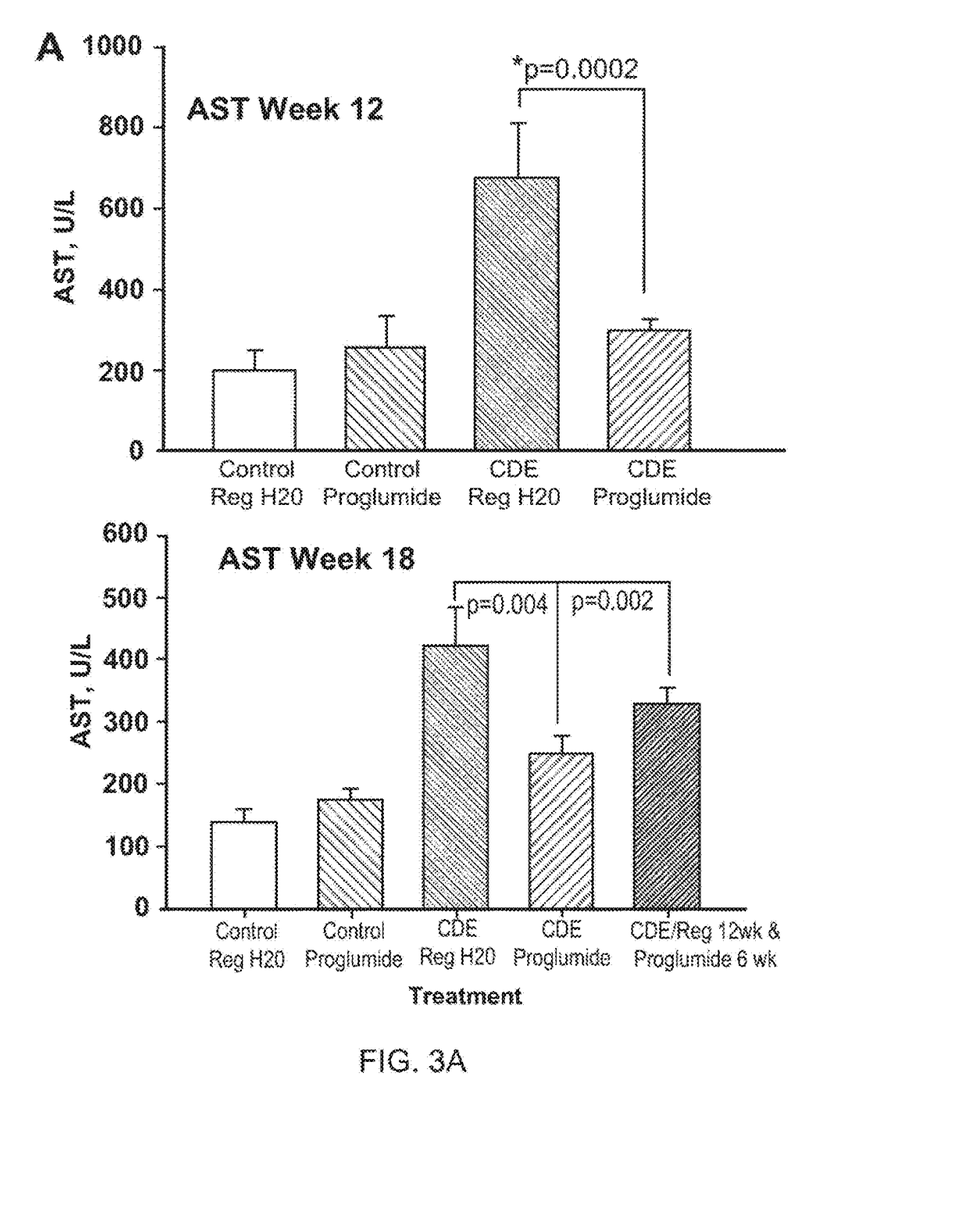
FIGS. 3A-3D show the results of serum blood liver tests for animals treated as outlined in FIG. 1.
Figure 3B:
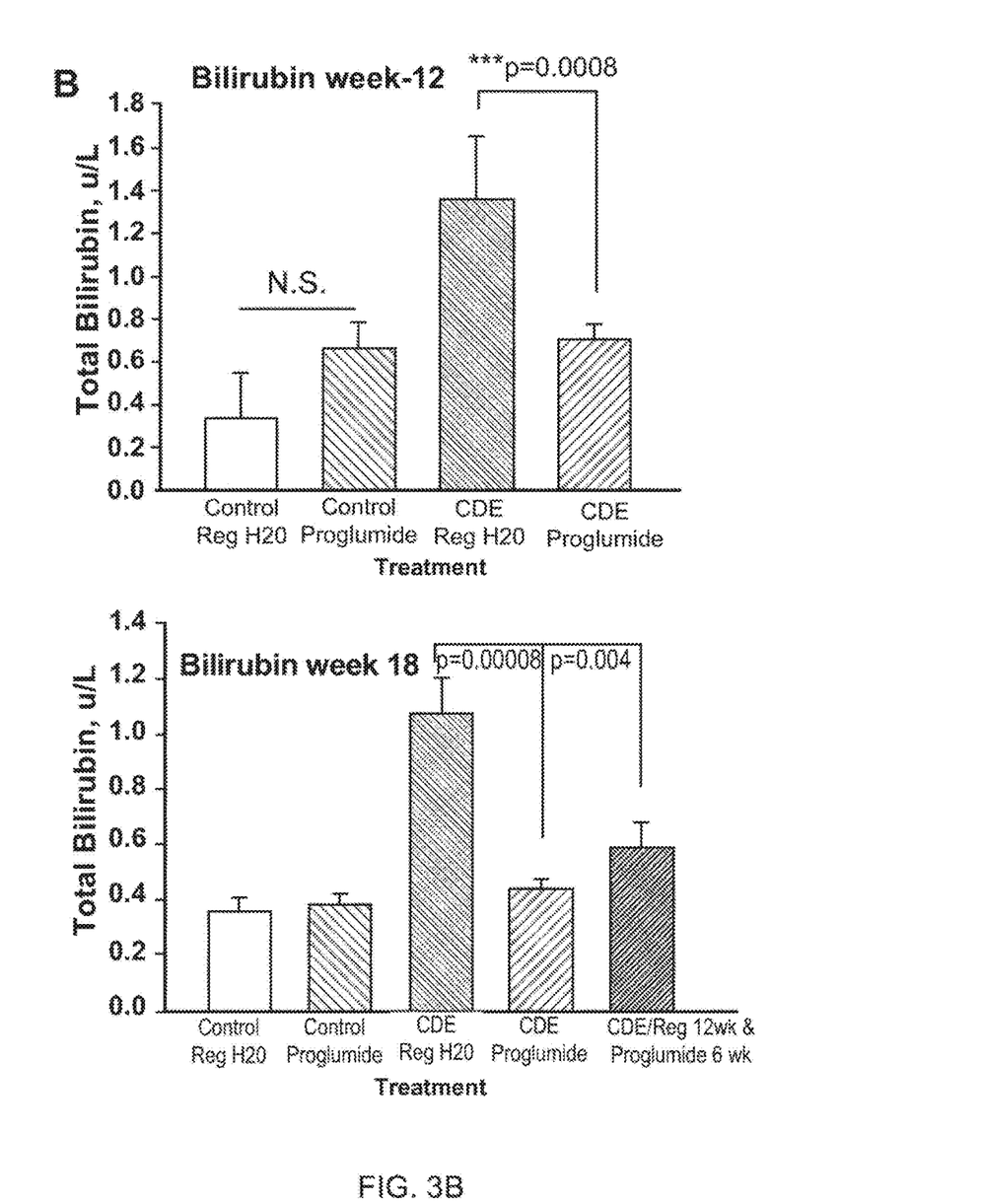
Figure 3C:
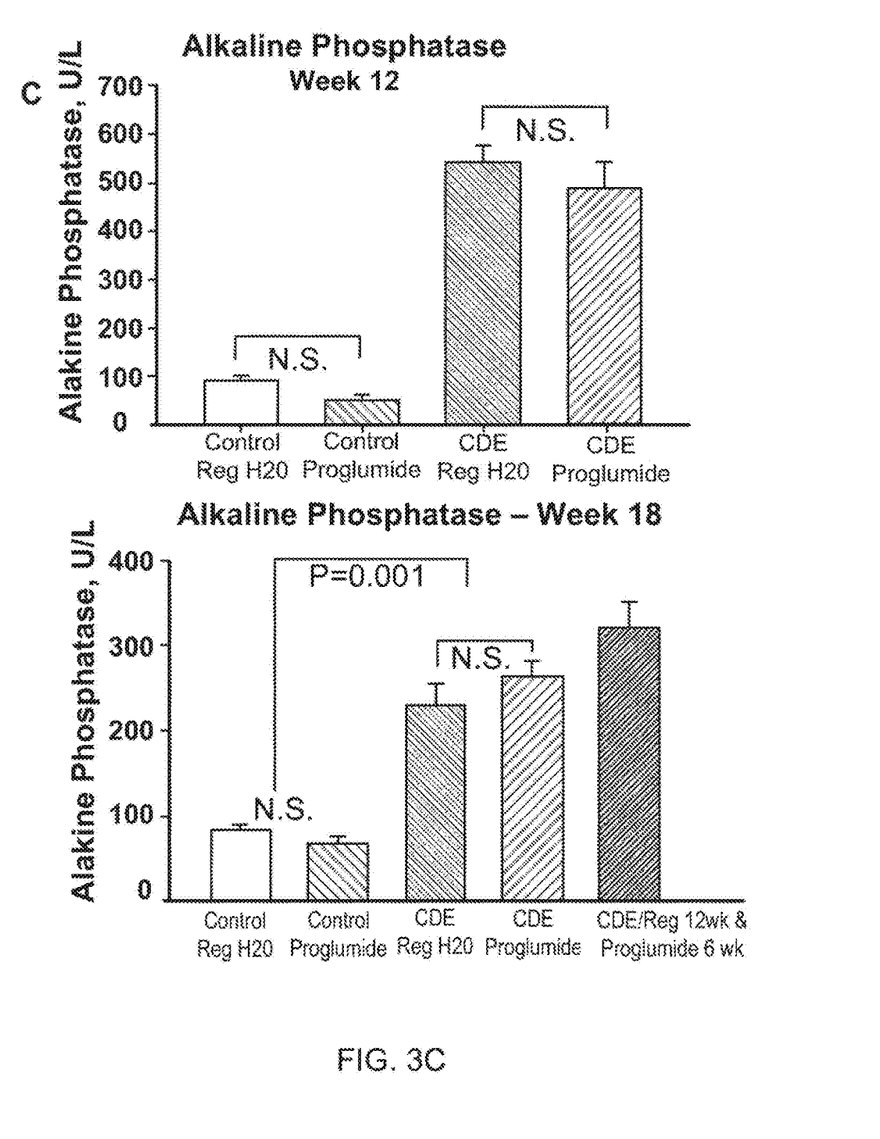
Figure 3D:
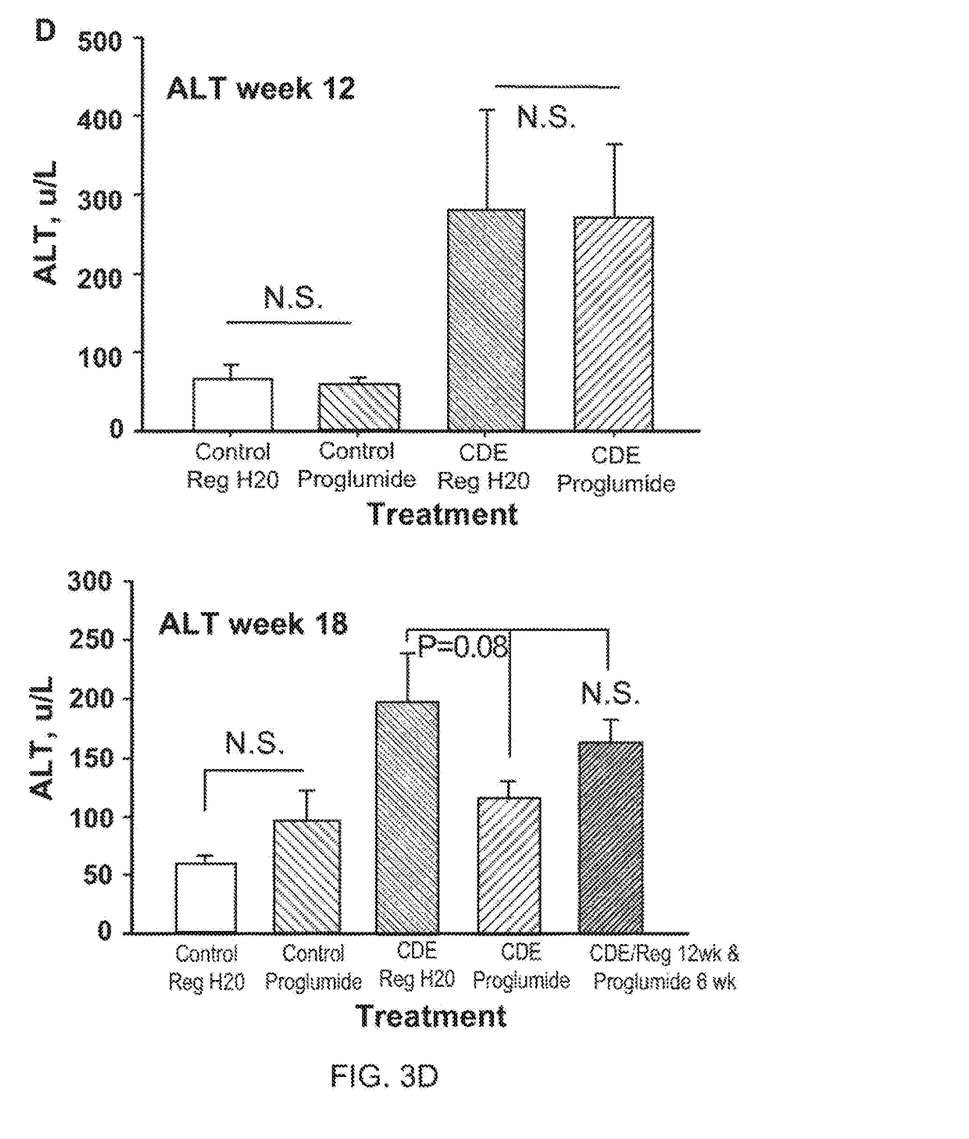

The animals on the high fat, control diet gained the most weight (FIG. 2A) compared to the other groups. The mice in the CDE/Reg group and the CDE-recovery group had significantly lower body weights at week 18 compared to all the other groups (FIG. 2A), likely because these mice have the greatest degree of liver injury. CCK receptors have been shown to play a role in satiety in the CNS. However, at the dose used in this study, proglumide-treated mice of the control group did not weigh more than the mice receiving untreated water. Although the proglumide-treated mice ate slightly more food than the mice receiving untreated water (FIG. 2B), this slight difference was not significant. Food intake overall in CDE-diet fed mice was less compared to mice on the choline-containing control diet (FIG. 2B). There was no difference in liver weights between any of the treatment groups. This figure shows that the response to proglumide in the CDE/proglumide-treated mice was not due to weight loss. This indicates that CCK-receptor blockade is effective in NASH independent of weight loss. Since the mice on the CDE/proglumide treatment actually ate more food than the CDE/regular mice, one would expect them to have more advanced liver disease, but instead they had less Proglumide Reverses Abnormal Blood Tests in CDE-Treated Mice Both the alanine aminotransferase and aspartate aminotransferases were increased in mice on the CDE/Reg diet and these values were restored to near normal with proglumide therapy, in spite of continuing on the CDE high fat diet (FIG. 3A and FIG. 3D). Proglumide did not prevent elevation of ALT blood levels at week 12 but did decrease ALT values after 18 weeks of therapy. Likewise, total bilirubin levels were elevated in mice fed the CDE/Reg diet (FIG. 3B) and the increased bilirubin was completely prevented by concomitant proglumide therapy. Bilirubin levels returned to the normal range in CDE-fed mice when proglumide was added as a recovery or rescue therapy after 12 weeks (FIG. 3B). Alkaline phosphatase levels increased in mice fed the CDE diet and this increase was not prevented or reversed by proglumide therapy (FIG. 3C).

CCK-Receptor Antagonist Prevents and Reverses Histologic Evidence of NASH

Figure 4A:
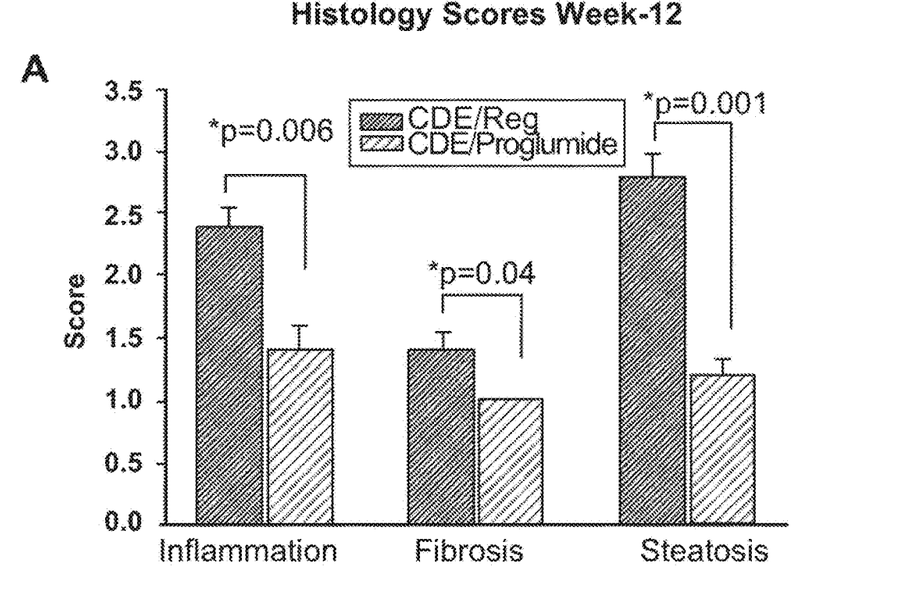
Figure 4B:
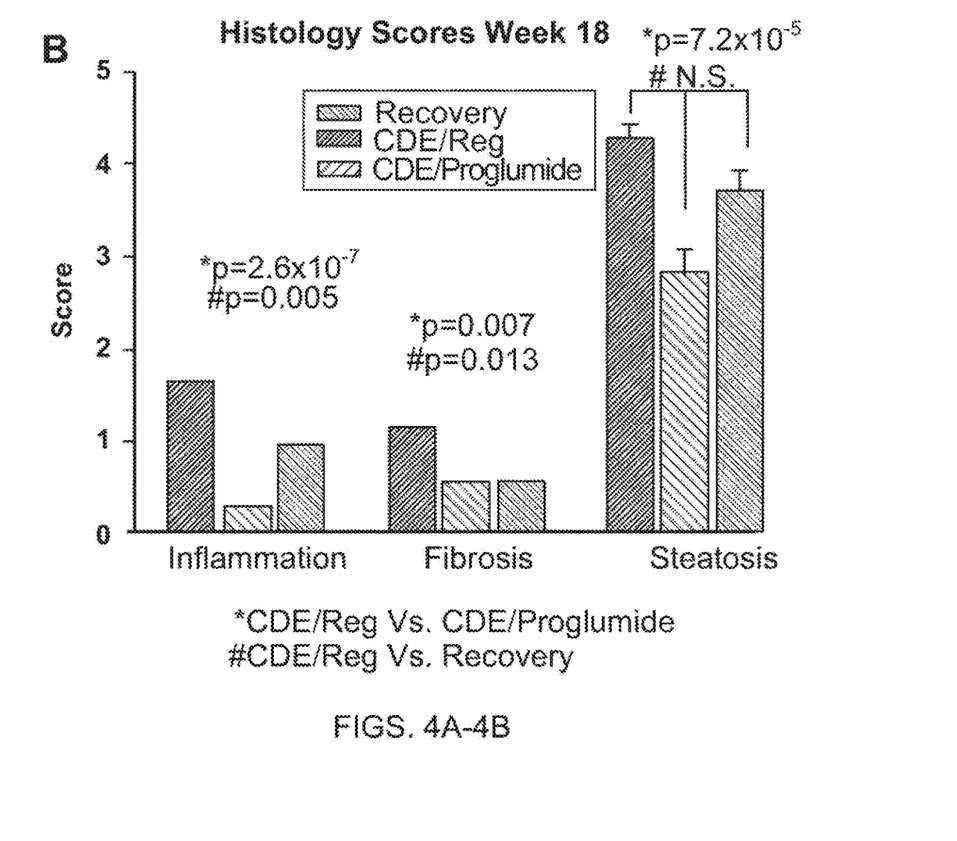
Figure 5A:
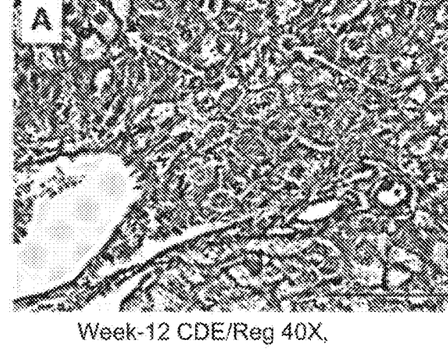
FIGS. 5A-5G show histological results from animals generated in the study outlined in FIG. 1.
Figure 5B:
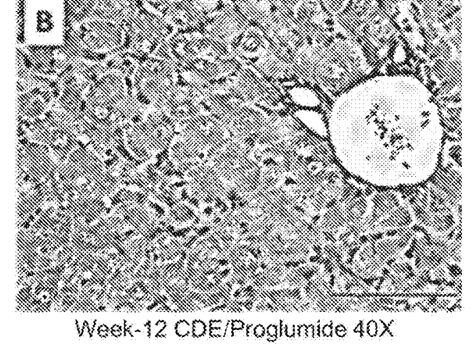

All three categories of histologic analysis including inflammation scores, fibrosis scores and steatosis scores improved in CDE mice given proglumide and also as a recovery therapy after NASH was evident at both week 12 (FIG. 4A) and week 18 (FIG. 4B). Even by week 12, liver histology of mice in the CDE/Reg group demonstrated evidence of fibrotic septa and balloon degeneration (FIG. 5A). In contrast, mice in the CDE/Prog treatment group histologically showed marked decrease in inflammation, minimal or no balloon degeneration and decreased steatosis and fibrosis as compared to untreated mice (FIG. 5B).

Proglumide Prevents NASH-Associated HCC

Figure 5C:
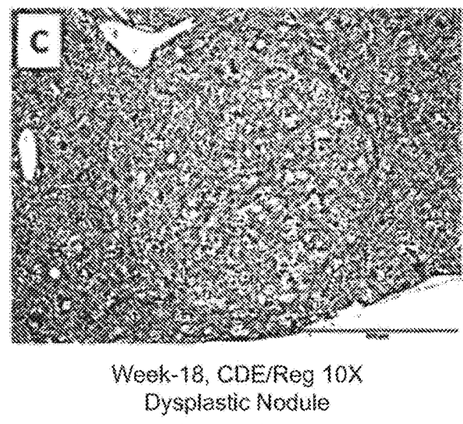
Figure 5D:
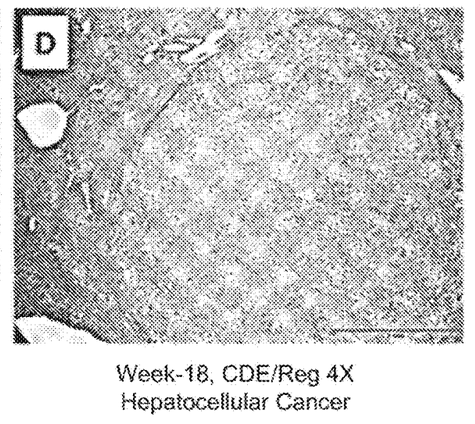

Only mice in the CDE/Reg-treatment group developed dysplastic nodules (FIG. 5C) or cancer (FIG. 5D). Of the 23 surviving mice in this group at week 18, two had overt hepatocellular cancer with more than one foci of cancer in each mouse liver. Six mice in the CDE/Reg group had dysplastic nodules at week 18. In contrast, none of the control mice or proglumide-treated mice had dysplastic nodules. Even the mice that were treated with CDE/Reg for 12 weeks (N=15) and then changed to CDE/proglumide for an additional 6 weeks had no evidence of HCC or dysplastic nodules.

Control Mice Developed NAFLD but not NASH

Figure 5E:
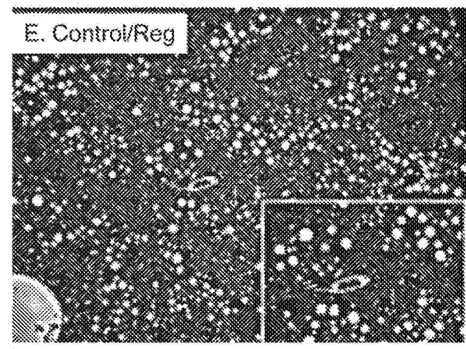
Figure 5F:
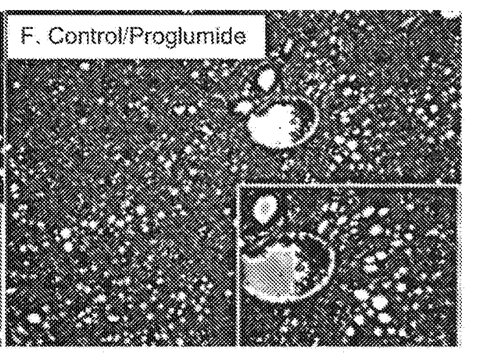
Figure 5G:
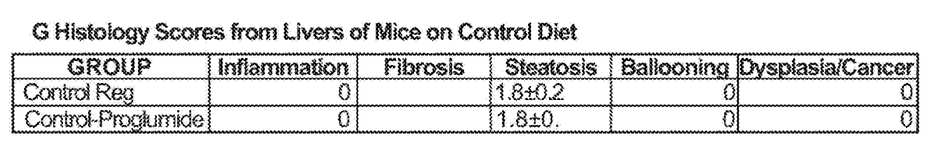

Mice on the control diets also had evidence of NAFLD but without any inflammation, fibrosis, and balloon degeneration. The pattern of steatosis in the mice fed either of the control high fat diet and untreated water (control/Reg; FIG. 5E) or mice on the control diet with proglumide in the drinking water (control/proglumide; FIG. 5F) was that of macrosteatosis, whereas the mice on the CDE diets had both macro- and microsteatosis. Histologic scoring for the control mice was zero in all categories per the pathologist with the exception of steatosis (FIG. 5G), and this pattern was consistent with NAFLD without NASH. No differences were noted in the liver histology between the control-diet mice with proglumide-treated water or untreated water.

The studies provided herein demonstrated that an orally administered CCK receptor antagonist can not only prevent NASH in mice on a CDE high fat Western diet but also can reverse the biochemical and histologic abnormalities of NASH once established. The therapy was nontoxic and the control mice exhibited no evidence of abnormalities in hepatic blood tests or weight as compared to control mice with untreated drinking water. These studies also showed that therapy with proglumide not only decreased inflammation and steatosis but it also decreased fibrosis. Neither Vitamin E nor pioglitazone have been shown to reverse fibrosis, the histologic precursor to cirrhosis. Another remarkable finding from this study was that none of the mice treated with proglumide developed dysplastic nodules or cancer at week-18. Thirty-five percent of the CDE-Reg treated mice (N=8 out of 23) developed dysplasia or HCC and none of the CDE/prog mice in the prevention arm (N=15) and none of the CDE/Reg+prog mice in the recovery treatment arm (N=15) developed dysplastic nodules or HCC.

In summary, these studies showed that proglumide prevented elevation of liver blood tests, and histologic changes consistent with NASH at weeks 12 and 18. In the reversal study, NASH was induced by the CDE diet and then mice were treated with proglumide for 6 weeks while continuing the CDE diet. Liver blood tests and histology improved significantly. Dysplastic nodules and HCC were found after 18-weeks only in mice on the CDE diet and untreated water; whereas, no dysplasia or HCC were found in proglumide-treated mice whether they received proglumide as prevention or as a rescue therapy.

The studies described herein also showed that proglumide decreased inflammation. It is possible that one of the mechanisms through which proglumide exhibits this anti-inflammatory property is through blockade of CCK receptors on immune cells and subsequent decrease in inflammatory cytokines. Little is known about the presence or action of CCK receptors on hepatocytes or hepatic stellate cells; however, since proglumide prevented and reversed histologic and biochemical hallmarks of NASH, these studies indicate that CCK receptors and CCK play a role in the pathogenesis of NASH and possibly development of HCC. Therefore, CCK-receptor blockade provides a novel and safe therapy for the treatment or prevention of NASH. A CCK receptor inhibitor, for example, proglumide, can also safely be used in subjects with diabetes, unlike vitamin E, because it does not increase the risk of bleeding.

What is claimed is:

1. A method for treating nonalcoholic steatohepatitis (NASH) in a subject, comprising administering to a subject having NASH an effective amount of a CCK receptor inhibitor, wherein the CCK receptor inhibitor is proglumide.

2. The method of claim 1, wherein the CCK receptor inhibitor decreases liver fibrosis in the subject.

3. The method of claim 1, wherein the subject has diabetes.

4. The method of claim 1, wherein the CCK receptor inhibitor decreases inflammation in the subject.

5. The method of claim 4, wherein the CCK receptor inhibitor decreases liver inflammation in the subject.

6. The method of claim 1, wherein administration of the CCK receptor inhibitor prevents hepatocellular carcinoma.

7. The method of claim 1, further comprising administering a second therapeutic agent to the subject, wherein the second therapeutic agent is metformin, pioglitazone, vitamin E or a statin.

8. A method for treating hepatic fibrosis in a subject comprising administering to a subject having hepatic fibrosis an effective amount of a CCK receptor inhibitor, wherein the CCK receptor inhibitor is proglumide.

9. The method of claim 8, further comprising administering a second therapeutic agent to the subject, wherein the second therapeutic agent is metformin, pioglitazone, vitamin E or a statin.

10. The method of claim 2, wherein the subject has diabetes.

* * * * *